United States Patent
Lin et al.

(10) Patent No.: US 11,422,618 B2
(45) Date of Patent: Aug. 23, 2022

(54) SMART STRAP AND METHOD FOR DEFINING HUMAN POSTURE

(71) Applicant: Acer Incorporated, New Taipei (TW)

(72) Inventors: Jia-Yu Lin, New Taipei (TW); Chih-Chiang Chen, New Taipei (TW)

(73) Assignee: Acer Incorporated, New Taipei (TW)

( * ) Notice: Subject to any disclaimer, the term of this patent is extended or adjusted under 35 U.S.C. 154(b) by 932 days.

(21) Appl. No.: 16/208,590

(22) Filed: Dec. 4, 2018

(65) Prior Publication Data

US 2020/0077926 A1    Mar. 12, 2020

(30) Foreign Application Priority Data

Sep. 6, 2018   (TW) .................... 107131373

(51) Int. Cl.
| | |
|---|---|
| *A61B 5/11* | (2006.01) |
| *G06F 3/01* | (2006.01) |
| *A61B 5/00* | (2006.01) |
| *A63B 24/00* | (2006.01) |
| *G06F 1/16* | (2006.01) |
| *A41D 1/00* | (2018.01) |
| *A45C 13/30* | (2006.01) |

(Continued)

(52) U.S. Cl.
CPC ............. *G06F 3/011* (2013.01); *A41D 1/002* (2013.01); *A45C 13/30* (2013.01); *A45F 3/14* (2013.01); *A61B 5/1116* (2013.01); *A61B 5/1128* (2013.01); *A61B 5/6823* (2013.01); *A61B 5/6831* (2013.01); *A63B 24/0062* (2013.01); *G06F 1/163* (2013.01); *G06F 3/017* (2013.01); *G06V 40/23* (2022.01); *A61B 5/6803* (2013.01)

(58) Field of Classification Search
CPC .......... G06F 3/011; G06F 1/163; G06F 3/017; A45F 3/14; A61B 5/1116; A61B 5/6831; A61B 5/6803; A61B 5/1128; A45C 13/30; G06K 9/00342; A63B 24/0062; A41D 1/002

See application file for complete search history.

(56) References Cited

U.S. PATENT DOCUMENTS

| | | |
|---|---|---|
| 2009/0229039 A1 | 9/2009 | Kuck et al. |
| 2010/0006611 A1 | 1/2010 | Knowles |

(Continued)

FOREIGN PATENT DOCUMENTS

| | | |
|---|---|---|
| CN | 105866949 | 8/2016 |
| CN | 106648116 | 5/2017 |

(Continued)

*Primary Examiner* — Abbas I Abdulselam
(74) *Attorney, Agent, or Firm* — JCIPRNET

(57) ABSTRACT

The disclosure provides a smart strap and a method for defining human posture. The smart strap includes a first shoulder strap, a second shoulder strap, a chest strap, a camera, and a microcontroller. Two ends of the chest strap are respectively connected to the first shoulder strap and the second shoulder strap, and the chest strap includes a stiffness segment. The camera is disposed on a surface of the stiffness segment, faces a first direction, and captures object images of an object on the first direction. The microcontroller receives the object images from the camera, detects a distance between the object and the camera based on the object images, and adjust a screen shown to a wearer of the smart strap according to the distance.

16 Claims, 13 Drawing Sheets

(51) Int. Cl.
*A45F 3/14* (2006.01)
*G06V 40/20* (2022.01)

(56) References Cited

U.S. PATENT DOCUMENTS

| | | | | |
|---|---|---|---|---|
| 2014/0225977 | A1* | 8/2014 | Vilcovsky | G06Q 30/00 |
| | | | | 348/14.07 |
| 2015/0127486 | A1 | 5/2015 | Advani | |
| 2017/0359569 | A1 | 12/2017 | Stafford | |
| 2019/0059748 | A1* | 2/2019 | Kaiser | A61B 7/04 |
| 2019/0265802 | A1* | 8/2019 | Parshionikar | G06F 3/012 |

FOREIGN PATENT DOCUMENTS

| | | |
|---|---|---|
| CN | 206470692 | 9/2017 |
| CN | 107977070 | 5/2018 |
| TW | I454966 | 10/2014 |
| TW | 201617787 | 5/2016 |

* cited by examiner

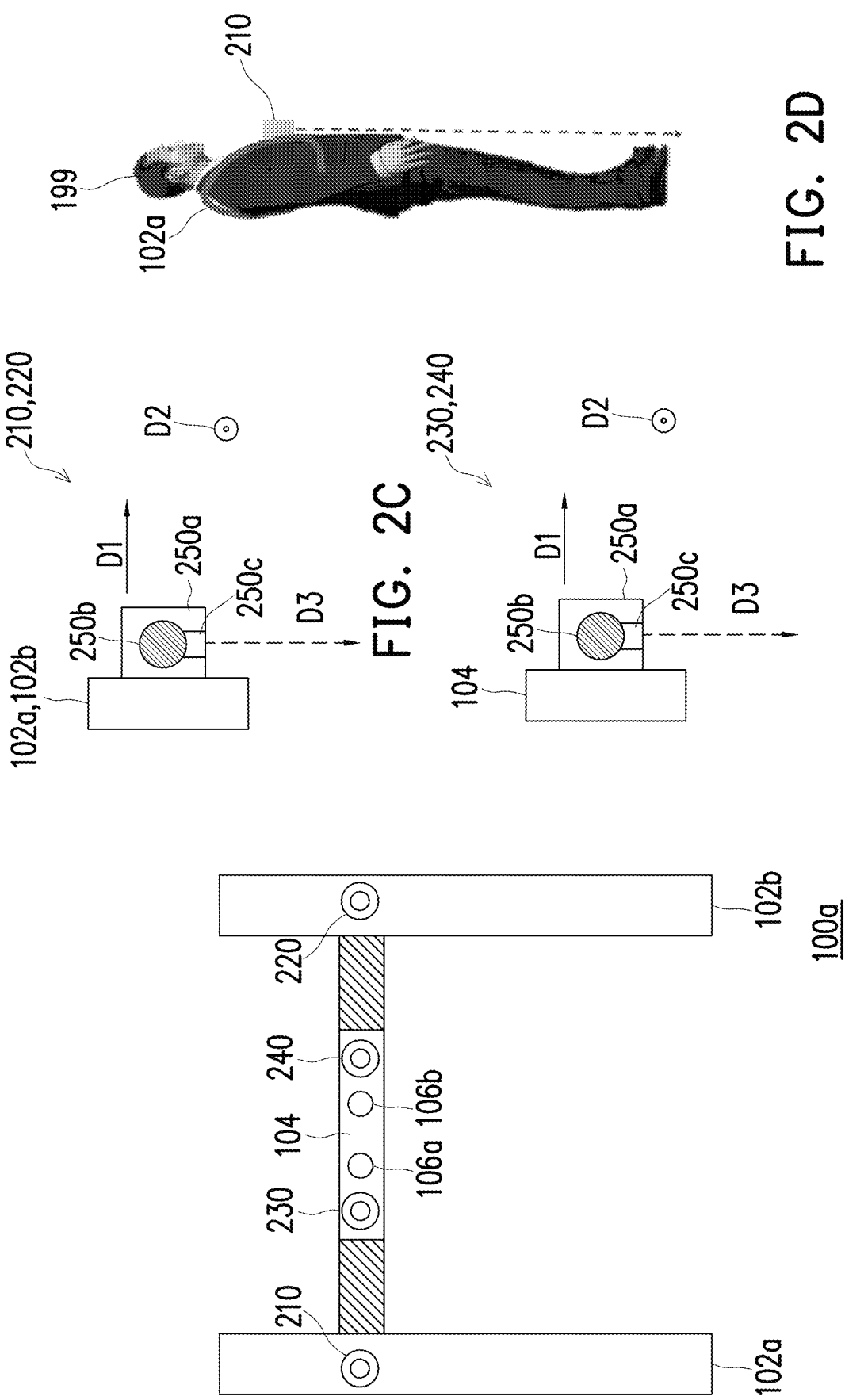

SMART STRAP AND METHOD FOR DEFINING HUMAN POSTURE

CROSS-REFERENCE TO RELATED APPLICATION

This application claims the priority benefit of Taiwan application serial no. 107131373, filed on Sep. 6, 2018. The entirety of the above-mentioned patent application is hereby incorporated by reference herein and made a part of this specification.

BACKGROUND OF THE INVENTION

1. Field of the Invention

The disclosure relates to a smart strap and a method for defining a human posture, and in particular to a smart strap and a method for defining a human posture based on the inside-out tracking technology.

2. Description of Related Art

With the maturity of virtual reality (VR) technology, consumers not only demand visual impacts, but also expect to further interact with VR content. Therefore, related technologies such as 3D sensing and face recognition have also become popular issues. Many input devices are currently available on the market, but most of them are embodied in the form of gloves or guns/weapons, etc., and it is relatively difficult to see practical applications of posture determination, such as determining the arm swinging posture. Although early detection devices (such as Kinect) for detecting the movement and movement of the user's limbs have been proposed by some manufactures, it is not convenient to use because such products require a large clearance area and distance to be recognized. Therefore, there are no further research and development plans.

In VR services, two optical positioning technologies, Phase Space and Light House, are often used to achieve position sensing for 3D moving objects. Both of the two technologies need to dispose positioning light source and receivers at specific locations in the environment and on the head-mounted display (HMD), wherein the difference therebetween is that the positioning light source of the Phase Space is disposed on the HMD, and the receiver of Light House is disposed on the HMD. However, both of the above methods belong to the Outside-in tracking type, that is, a camera or an infrared light source is required to be used in the external environment to communicate with the target (HMD/human body).

However, Outside-in tracking generally has the following disadvantages: (1) higher cost—additional hardware such as track, camera or infrared light source is needed; (2) higher environmental demand—the environment needs to be large and have a clearance area, making it difficult for people to prepare a clearance area dedicated for VR activities; (3) difficult to be installed—people may need to drill holes or nails in the surrounding environment; (4) low convenience—the above technologies can only be used in a well-installed environment, and the installations require high calibration skills.

In contrast, the Inside-out tracking technology can determine the external situation only through the wearable device worn by the human body, so none of the above mentioned problems will occur. Therefore, it is important for those skilled in the art to develop better inside-out tracking technologies.

SUMMARY OF THE INVENTION

Accordingly, the present disclosure is directed to a smart strap and a method of defining a human posture which may be used to solve the above technical problems.

The disclosure provides a smart strap including a first shoulder strap, a second shoulder strap, a chest strap, at least one camera, and a microcontroller. The chest strap has a first end and a second end, wherein the first end of the chest strap is connected to the first shoulder strap, the second end of the chest strap is connected to the second shoulder strap, and the chest strap comprises a stiffness segment. The at least one camera is disposed on a surface of the stiffness segment and facing a first direction, capturing a plurality of object images of an object in the first direction. The microcontroller is connected to the at least one camera, receives the object images from the at least one camera, detects a distance between the object and the at least one camera based on the object images, and adjusts a screen shown to a wearer of the smart strap according to the distance.

The disclosure provides a smart strap including a first shoulder strap, a second shoulder strap, a chest strap, a plurality of posture detecting modules, and a microcontroller. The chest strap has a first end and a second end, wherein the first end of the chest strap is connected to the first shoulder strap, and the second end of the chest strap is connected to the second shoulder strap. The plurality of posture detecting modules are symmetrically disposed on the first shoulder strap and the second shoulder strap, or symmetrically disposed on the chest strap, wherein each of the posture detecting modules is configured to detect a distance variation in a specific direction. The microcontroller is connected to the posture detecting modules and defining a human posture of a wearer of the smart strap according to the distance variation detected by each of the posture detecting modules.

The disclosure provides a method of defining a human posture, adapted to a smart strap comprising a first shoulder strap, a second shoulder strap, a chest strap, a plurality of posture detecting modules, and a microcontroller. The method includes: detecting a distance variation in a specific direction by each of the posture detecting modules, wherein the posture detecting modules are symmetrically disposed on the first shoulder strap and the second shoulder strap, or symmetrically disposed on the chest strap; and defining a human posture of a wearer of the smart strap according to the distance variation detected by each of the posture detecting modules.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

FIG. 2B is a front view of a smart strap according to the second embodiment of the present disclosure.

FIG. 2C is a side view of the posture detecting module disposed on the first shoulder strap or the second shoulder strap according to FIG. 2B.

FIG. 2D is a side view of the wearing scenario of the smart strap according to FIG. 2C.

FIG. 2E is a side view of the posture detecting module disposed on the stiffness segment according to FIG. 2B.

DESCRIPTION OF THE EMBODIMENTS

Figure 1A:
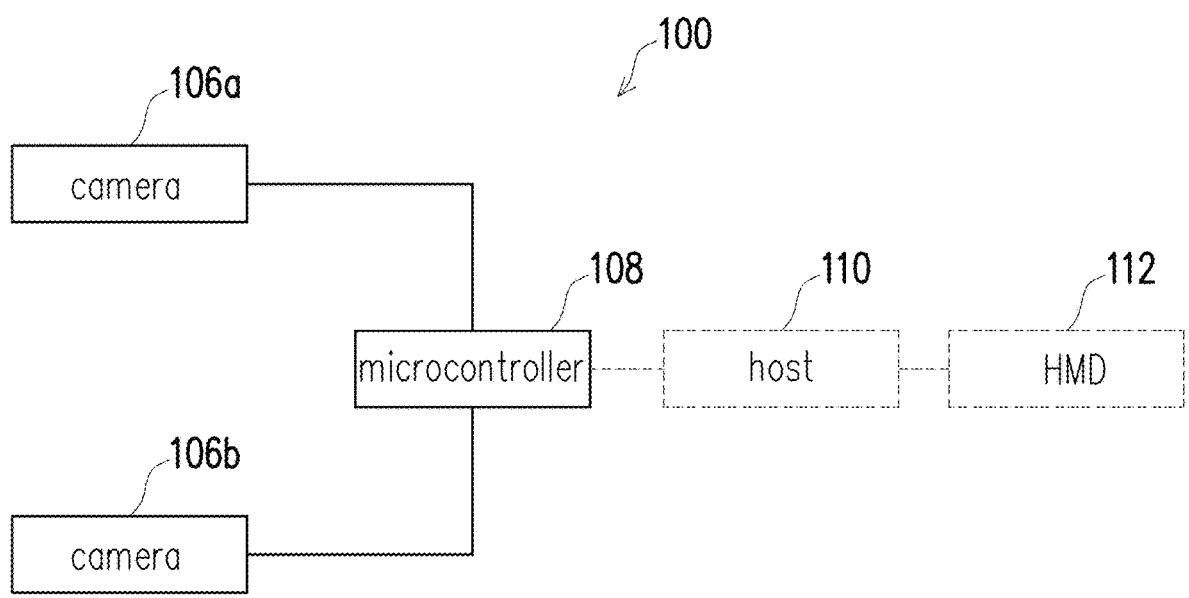
FIG. 1A is a system architecture diagram according to a first embodiment of the present disclosure.

Reference will now be made in detail to the present preferred embodiments of the disclosure, examples of which are illustrated in the accompanying drawings. Wherever possible, the same reference numbers are used in the drawings and the description to refer to the same or like parts.

Figure 1B:
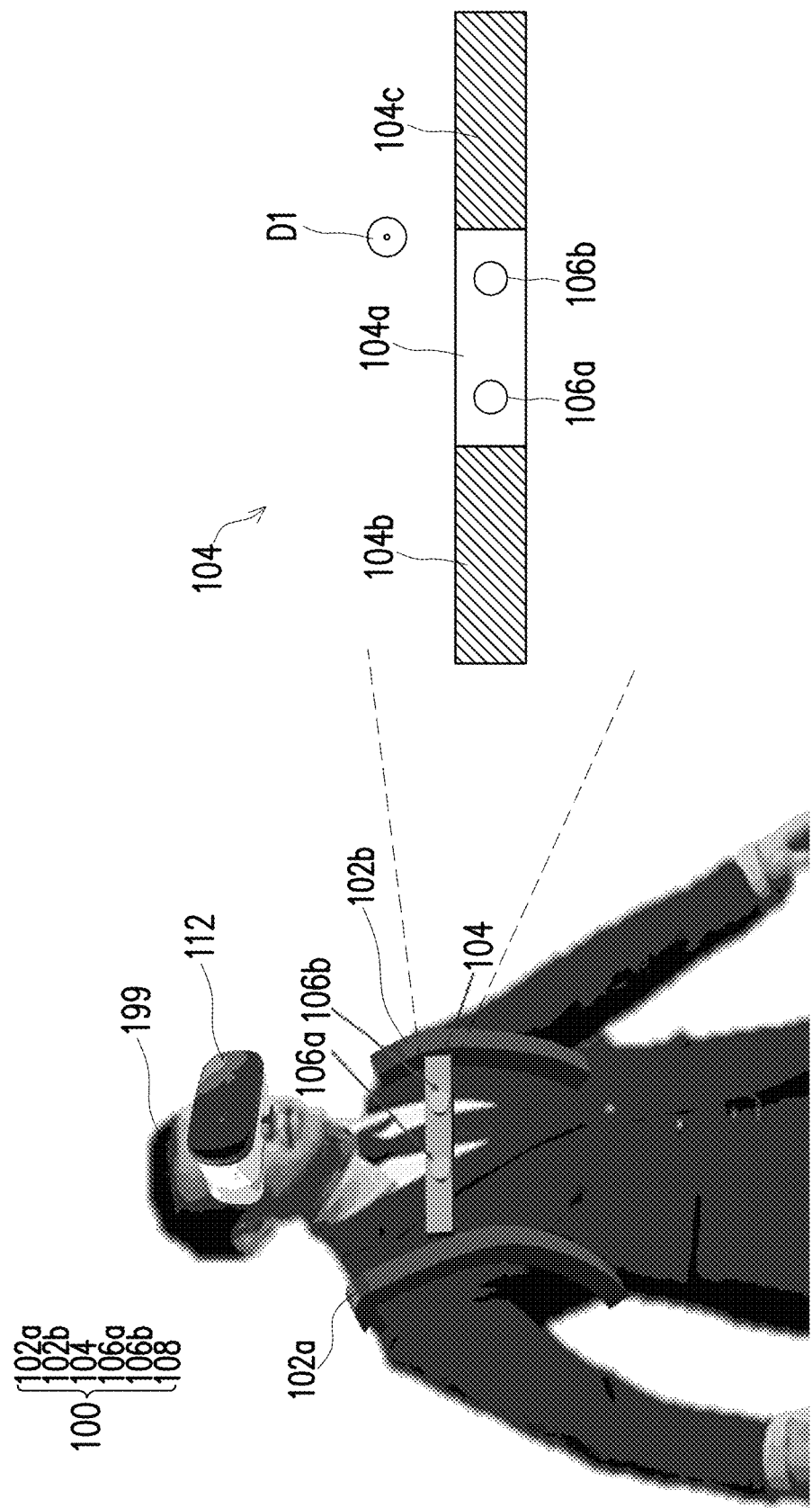
FIG. 1B is a wearing scenario according to FIG. 1A.

See FIG. 1A and FIG. 1B, wherein FIG. 1A is a system architecture diagram according to a first embodiment of the present disclosure, and FIG. 1B is a wearing scenario according to FIG. 1A. In the first embodiment, a system 10 includes a smart strap 100, a host 110, and an HMD 112. The smart strap 100 can be worn on the wearer 199 as shown in FIG. 1B and can perform detections by various sensing elements on the smart strap 100, and the detected signals and/or data are fed back to the host 110, such that the host 110 may accordingly control the HMD 112 to provide a screen (e.g., VR content) to the wearer 199 for viewing. In various embodiments, the host 110 may be a personal computer, a backpack computer, or other devices that can be used to transfer signals between the smart strap 100 and the HMD 112 and control the display of the HMD 112, but the disclosure is not limited thereto.

As shown in FIGS. 1A and 1B, the smart strap 100 includes a first shoulder strap 102a, a second shoulder strap 120b, a chest strap 104, cameras 106a, 106b, and a microcontroller 108. For facilitating the following discussions, it is assumed that the first shoulder strap 102a is worn on the right shoulder of the wearer 199 and the second shoulder strap is worn on the left shoulder of the wearer 199, but the disclosure is not limited thereto.

The chest strap 104 has a first end and a second end, wherein the first end of the chest strap 104 is connected to the first shoulder strap 102a and the second end of the chest strap 104 is connected to the second shoulder strap 102b. In the first embodiment, the chest strap 104 includes a stiffness segment 104a, which can be understood as a segment that is not elastic and does not deform due to external forces. In addition, in order to make the smart strap 100 suitable for being worn on the wearer 199 having various body shapes, the chest strap 104 may be disposed with elastic segments 104b and 104c, wherein the elastic segment 104b may be connected between the stiffness segment 104a and the shoulder straps 102a, and the elastic segment 104c can be connected between the stiffness segment 104a and the second shoulder strap 102b for expansion and control movement along with the body shape of the wearer 199.

The cameras 106a and 106b are disposed on the surface of the stiffness segment 104a and face a first direction D1 (for example, the front of the wearer 199). Accordingly, the cameras 106a and 106b can capture a plurality of object images of an object located in the first direction D1 (e.g., an object located in front of the wearer 199).

The microcontroller 108 is coupled to the cameras 106a and 106b and receives the object images from the cameras 106a and 106b. The distance between the object and the cameras 106a and 106b is detected based on the object images, and the microcontroller 108 adjusts the screen shown to the wearer 199 of the smart strap 100 according to the distance.

In the first embodiment, the mechanism by which the microcontroller 108 detects the aforementioned distance based on the object images captured by the cameras 106a and 106b can be referred to the Taiwan Patent Application No. 107121782, which is incorporated herein in its entirety by reference. Moreover, since the cameras 106a and 106b are disposed on the stiffness segment 104a which is not elastic and does not deform, the relative distance between the cameras 106a and 106b can be maintained. In this case, the distance detected by the microcontroller 108 based on the object images can be more accurate. Since the microcontroller 108 can transmit the detected distance to the host 110 and the HMD 112 to adjust the screen provided to the wearer 199, the aforementioned screen can be rendered to have a better visual effect, thereby improving the user experience.

From another point of view, since the smart strap 100 can detect the distance to assist in adjusting the screen provided to the wearer 199, it can be regarded as providing effects of upgrading the VR experience to the augmented reality (AR) or mixed reality (MR) through the inside-out tracking technology.

In other embodiments, the aforementioned mechanism for the smart strap 100 to detect the distance can also be implemented via, for example, Time of Flight (ToF), structure light, or stereo camera, but the disclosure is not limited thereto.

Figure 2A:
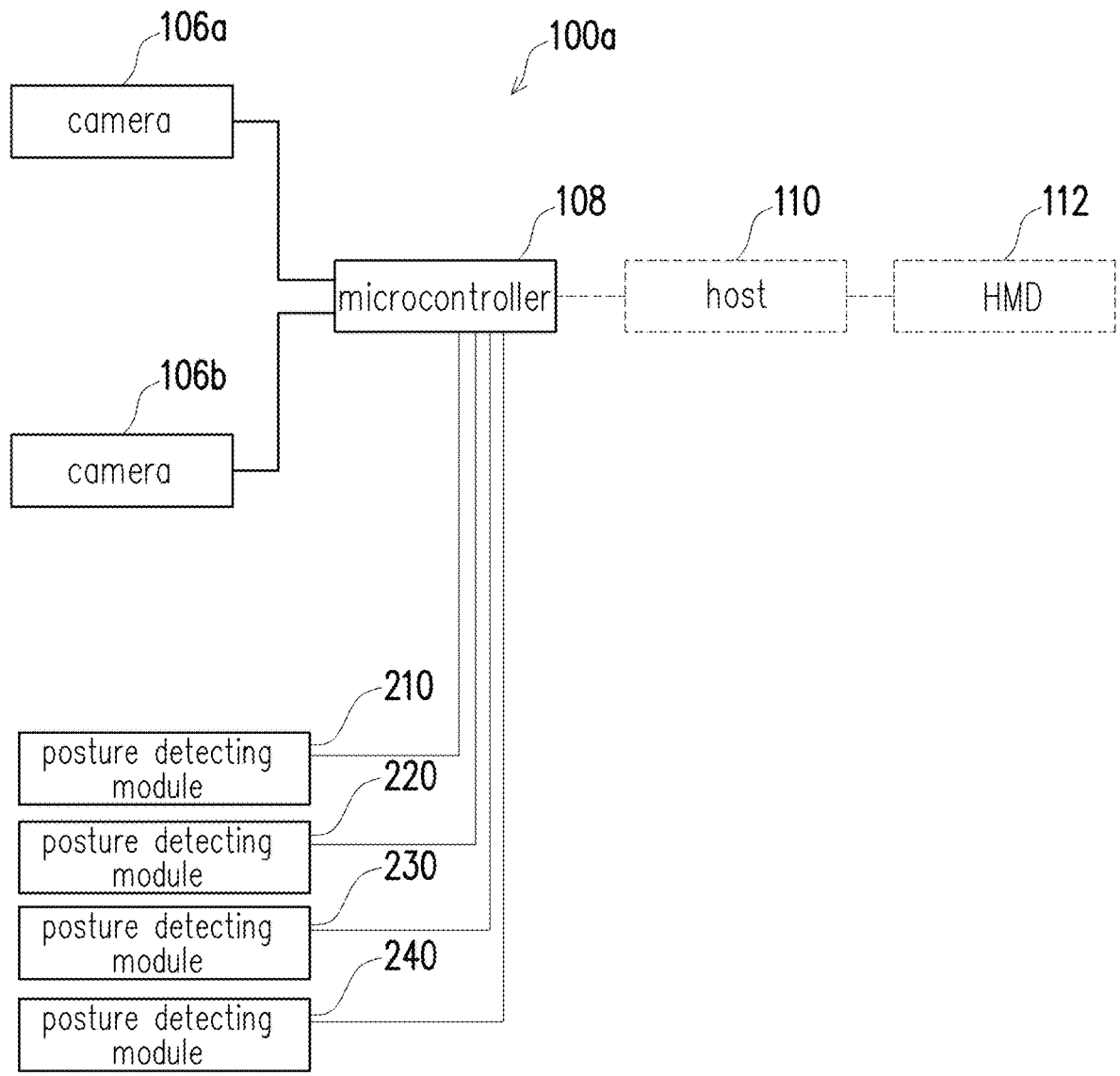
FIG. 2A is a system architecture diagram of a second embodiment of the present disclosure.

See FIGS. 2A and 2B, wherein FIG. 2A is a system architecture diagram according to a second embodiment of the present disclosure, and FIG. 2B is a front view of the smart strap according to the second embodiment of the present disclosure. Compared with the first embodiment, the smart strap 100a of the second embodiment further includes posture detecting modules 210, 220, 230 and 240 coupled to the microcontroller 108. As shown in FIG. 2B, the posture detecting modules 210 and 220 can be symmetrically disposed at two locations corresponding to each other on the first shoulder strap 102a and the second shoulder strap 102b for detecting the human posture of the wearer of the smart strap 100a. Similarly, the posture detecting modules 230 and 240 can be symmetrically disposed at two locations corresponding to each other on the stiffness segment 104a for detecting the human posture of the wearer of the smart strap 100a. In the second embodiment, the architecture and operation principle of the posture detecting modules 210, 220, 230, and 240 are similar, which will be discussed in accompanying with FIG. 2C.

See FIG. 2C, which is a side view of the posture detecting module disposed on the first shoulder strap or the second shoulder strap according to FIG. 2B. As shown in FIG. 2C, each of the posture detecting modules 210 and 220 can include a base 250a, a knob 250b, and a distance sensor 250c. The base 250a includes a bottom surface, a side surface and a top surface, wherein the bottom surface of the base 250a is connected to the surface of the first shoulder strap 102a or the surface of the second shoulder strap 102b, and the top surface of the base 250a faces the first direction D1. The knob 250b includes a bottom surface, a side surface, and a top surface, wherein the bottom surface of the knob 250a is rotatably connected to the side surface of the base 250a, and the top surface of the knob 250b faces the second direction D2, wherein the second direction D2 is perpendicular to the first direction D1. The distance sensor 250c is disposed on the side surface of the knob 250b and performs distance detection in different directions in response to the rotation of the knob 250b.

In an embodiment, if the wearer is of a medium build, when the smart strap 100a is worn on the wearer's body, the distance sensor 250c should be able to perform distance detection in the third direction D3 (e.g., vertically downward) in the manner shown in FIG. 2C.

However, in other embodiments, if the wearer's body is relatively big, the distance sensor 250c may be changed accordingly to detect in other directions. In this case, the wearer can adjust the third direction D3 that the distance sensor 250c performs the distance detection by, for example, rotating the knob 250b according to the instruction in the VR content, but the present disclosure is not limited thereto.

See FIG. 2D, which is a side view of the wearing scenario of the smart strap according to FIG. 2C. In this embodiment, since the first shoulder strap 102a is worn on the right shoulder of the wearer 199, the distance sensor (not shown) of the posture detecting module 210 performs distance detection vertically downward. Therefore, when the wearer lifts the right knee, the distance sensor of the posture detecting module 210 will detect the distance variation accordingly. Similarly, when the user lifts the left knee, the distance sensor on the second shoulder strap 102b can also detect the distance variation accordingly.

In one embodiment, the distance sensors of the posture detecting modules 210 and 220 can respectively transmit the detected first specific distance and the second specific distance to the microcontroller 108, such that the microcontroller 108 may know that whether the knee of the wearer 199 has been raised based on the variations of the first specific distance and the second specific distance, but the disclosure is not limited thereto.

See FIG. 2E, which is a side view of the posture detecting module disposed on the stiffness segment according to FIG. 2B. In this embodiment, the posture detecting modules 230 and 240 are structurally and operationally identical to the posture detecting modules 210 and 220 except that the locations are different from those of the posture detecting modules 210 and 220 of FIG. 2C. Therefore, the relevant details will not be repeated here.

Figure 3:
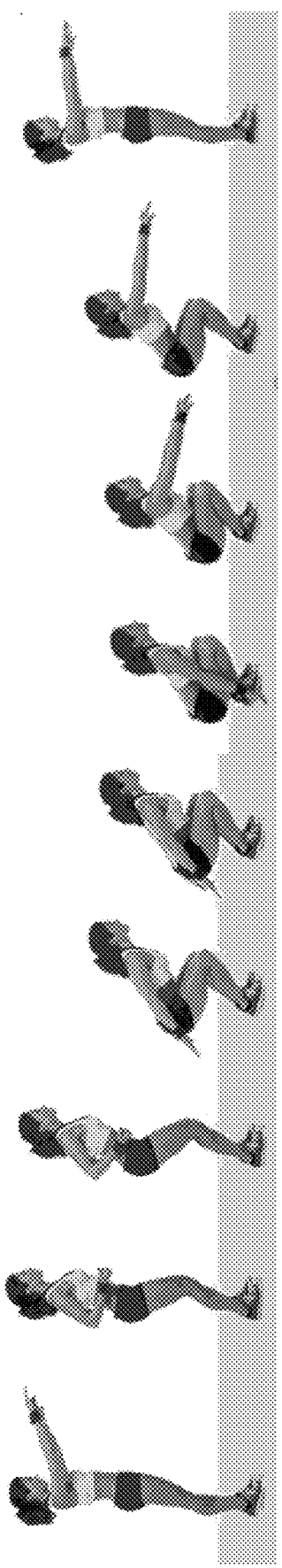
FIG. 3 is a schematic diagram of a specified movement according to the second embodiment of the present disclosure.

See FIG. 3, which is a schematic diagram of a specified movement according to a second embodiment of the present disclosure. In the present embodiment, the continuous movement shown in FIG. 3 can be viewed as the VR content provided to the wearer 199 of the smart strap 100a of the second embodiment to request the wearer 199 to do the same movement as that of FIG. 3 (e.g., a movement of squatting down and standing up). During the wearer 199 performing the specified movement according to FIG. 3, the posture detecting modules 210 and 220 (or the posture detecting modules 230 and 240) can obtain the calibration reference value dedicated to the wearer 199 according to the measured distance variation. For example, after the wearer 199 squats down, the distance measured by the posture detecting modules 210 and 220 (for example, 50 cm) corresponds to the squatting posture of the wearer 199, and the distance can be set as the calibration reference value accordingly. Therefore, when the posture detecting modules 210 and 220 measure the distance equal to the calibration reference value again, the microcontroller 108 can know that the wearer 199 is currently presenting the squatting posture. For another example, after the wearer 199 stands up, the distance measured by the posture detecting modules 210 and 220 (for example, 150 cm) corresponds to the standing posture of the wearer 199, and the distance can be set as the calibration reference value accordingly. Therefore, when the posture detecting modules 210 and 220 measure the distance equal to the calibration reference value again, the microcontroller 108 can know that the wearer 199 is currently presenting the standing posture.

Figure 4:
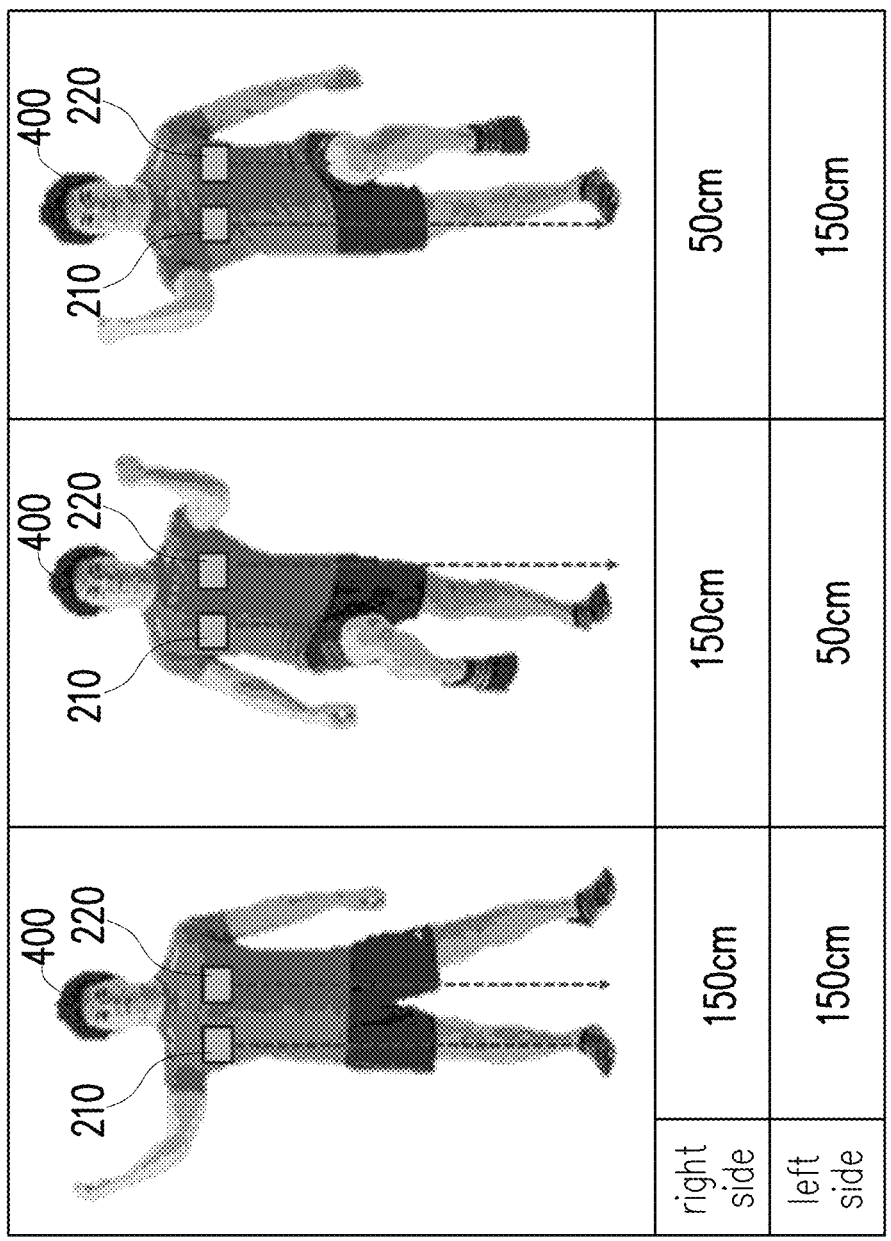
FIG. 4 is a schematic diagram of detecting a human posture according to the second embodiment of the present disclosure.

Please refer to FIG. 4, which is a schematic diagram of detecting a human posture according to the second embodiment of the present disclosure. In the present embodiment, it is assumed that the wearer 400 is wearing the smart strap 100a (not shown) of FIG. 2B, and the smart strap 100a has obtained the calibration reference value (for example, 150 cm) of the wearer 400 in the standing posture through the mechanism shown in FIG. 3. Therefore, when the posture detecting modules 210 and 220 respectively located on the right and left sides of the wearer 400 detect 150 cm, the microcontroller 108 can know that the wearer 400 is currently in the standing posture.

In addition, if the first specific distance (for example, 50 cm) detected by the posture detecting module 210 is smaller than the second specific distance detected by the posture detecting module 220 (for example, 150 cm), the microcontroller 108 can know that the right knee of the wearer 400 has been lifted. Conversely, if the first specific distance (for example, 150 cm) detected by the posture detecting module 210 is greater than the second specific distance (for example, 50 cm) detected by the posture detecting module 220, the microcontroller 108 can know that the left knee of the wearer 400 has been lifted, but the present disclosure is not limited thereto.

Figure 5:
FIG. 5 is a schematic diagram of adjusting a viewing angle of a screen according to the second embodiment of the present disclosure.
Figure 5:
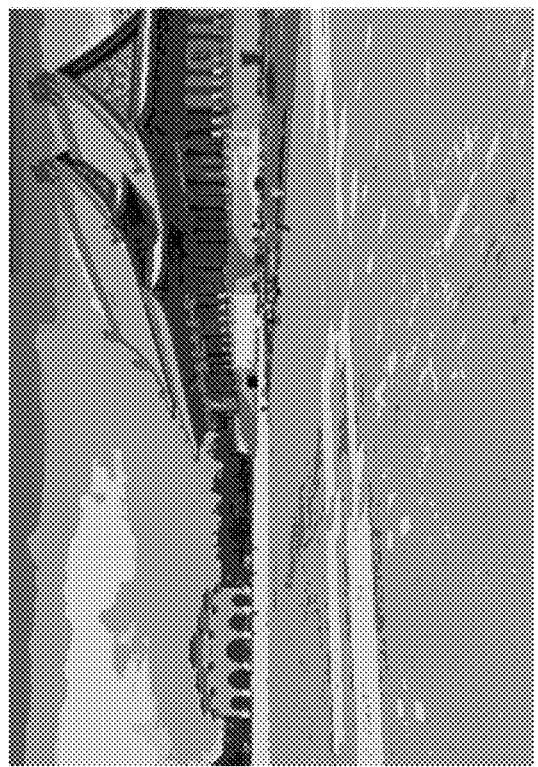

Please refer to FIG. 5, which is a schematic diagram of adjusting a viewing angle of a screen according to the second embodiment of the present disclosure. In this embodiment, when the wearer wears the smart strap 100a shown in FIG. 2B, the microcontroller 108 can adjust the height of the viewing angle provided to the wearer according to the variations of the first specific distance and the second specific distance detected by the posture detecting modules 210 and 220 (or the posture detecting modules 230 and 240). For example, the microcontroller 108 can derive the height of the wearer according to the first specific distance and the second specific distance measured when the wearer is in the standing posture, and accordingly increase or decrease the viewing angle of the screen of the VR content. If the wearer's height is short, the microcontroller 108 can adjust the viewing angle of the screen of the VR content to the low viewing angle shown on the left of FIG. 5 accordingly. Conversely, if the height of the wearer is high, the microcontroller 108 can adjust the viewing angle of the screen of the VR content to the high viewing angle shown on the right side of FIG. 5 accordingly, but the present disclosure is not limited thereto.

As can be known from the above, by providing a plurality of posture detecting modules, the smart strap of the present disclosure can further have the functions of detecting the posture of the wearer, thereby providing effects of upgrading the VR experience to AR or MR through the inside-out tracking technology. Moreover, the viewing angle provided to the wearer can be changed according to the distance measured by the posture detecting module, so that the screen seen by the wearer in the VR content can be more closely related to the scene seen in real life, and the user experience can be improved.

In addition, there is a projection technique in the prior art which can be used as a reference point for virtual image projection by placing a specific illuminating sphere on the ground. In this way, the projected virtual character can be presented at an appropriate height and position. However, the present disclosure can achieve the same effect without the above-mentioned illuminating sphere, thereby reducing the associated implementation cost and complexity.

Figure 6:
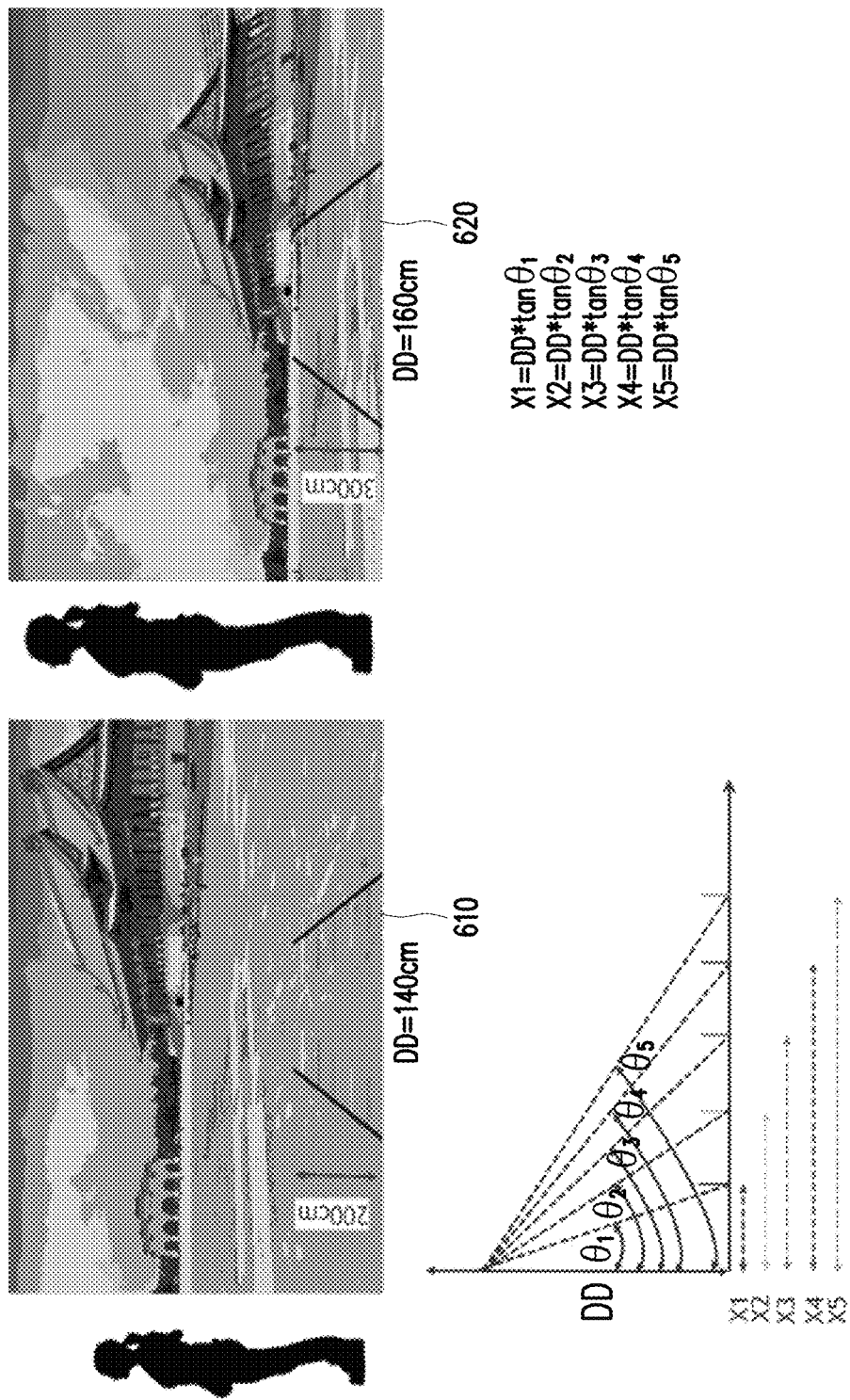
FIG. 6 is a schematic diagram of displaying a visual aid grid in a screen according to the second embodiment of the present disclosure.

Please refer to FIG. 6, which is a schematic diagram of displaying a visual aid grid in a screen according to the second embodiment of the present disclosure. In this embodiment, after the first specific distance and the second specific distance (hereinafter referred to as the distance DD) respectively measured by the posture detecting modules 210 and 220 (or the posture detecting modules 230 and 240), the microcontroller 108 can calculate the actual distances corresponding to the distances X1, X2, X3, X4, and X5 be according to preset angles $\theta_1$, $\theta_2$, $\theta_3$, $\theta_4$, $\theta_5$ and accordingly adjust the visual aid grids 610 and 620 presented to the wearer in the VR content for the wearer's reference.

For example, assuming that the distance DD is 140 cm, its corresponding visual aid grid 610 can be as shown at the upper left of FIG. 6. In the present embodiment, the visual aid grid 610 may include a plurality of grid lines, wherein the grid lines from near to far may respectively correspond to the distances X1 to X5 calculated based on the distance DD (i.e., 140 cm). Thereby, it is easier for the wearer to judge the relative distance in the VR content through the visual aid grid 610.

For another example, assuming that the distance DD is 160 cm, the corresponding visual aid grid 620 can be as shown in the upper right of FIG. 6. In the present embodiment, the visual aid grid 620 may include a plurality of grid lines, wherein the grid lines from near to far may respectively correspond to the distances X1-X5 calculated based on the distance DD (i.e., 160 cm). Thereby, it is easier for the wearer to judge the relative distance in the VR content through the visual aid grid 620.

Figure 7A:
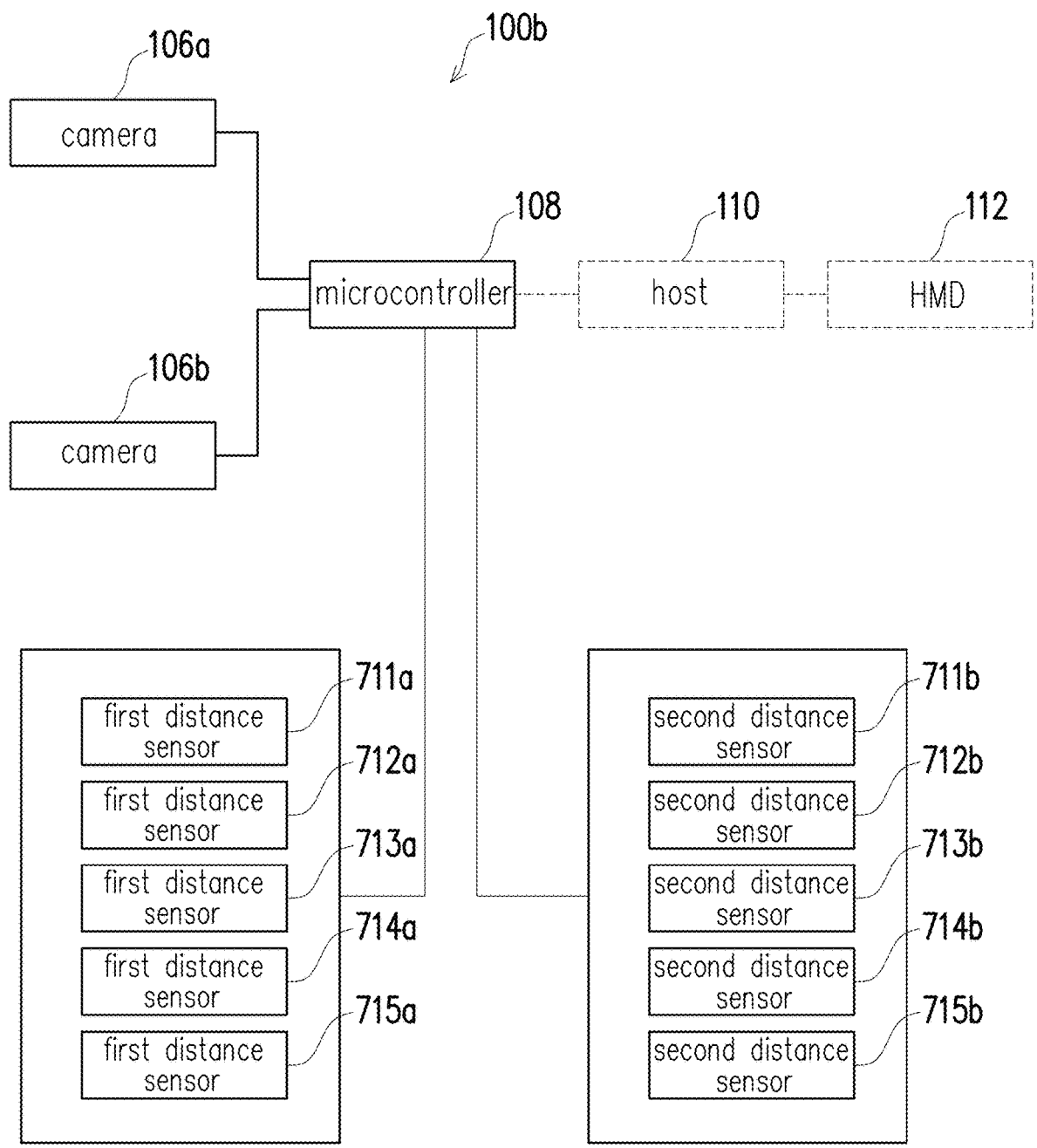
FIG. 7A is a system architecture diagram according to a third embodiment of the present disclosure.
Figure 7B:
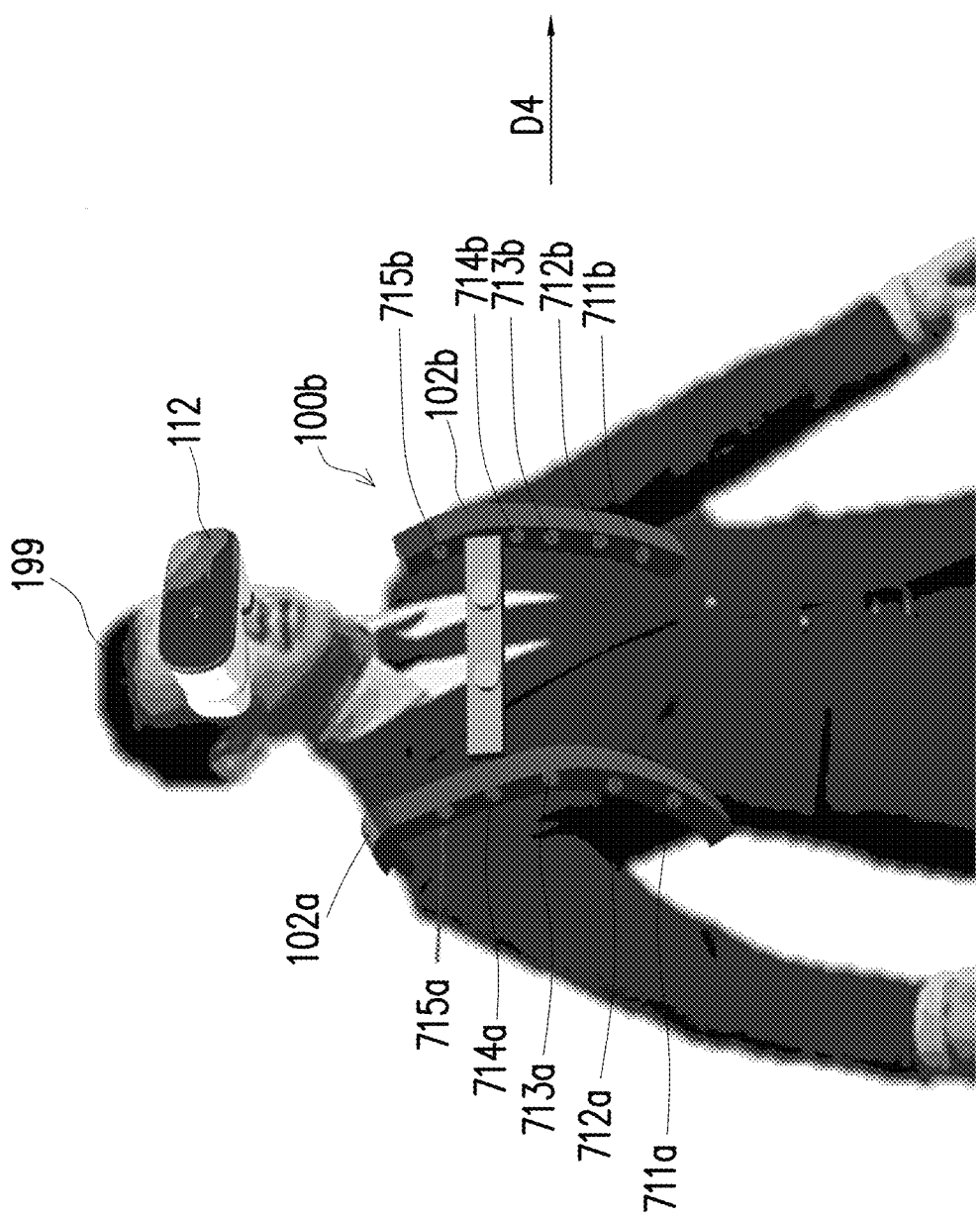
FIG. 7B is a wearing scenario of a smart strap according to the third embodiment of the present disclosure.

See FIG. 7A and FIG. 7B, wherein FIG. 7A is a system architecture diagram according to a third embodiment of the present disclosure, and FIG. 7B is a wearing scenario of the smart strap according to the third embodiment of the present disclosure. Compared with the first embodiment, the smart strap 100b of the third embodiment further includes a plurality of first distance sensors 711a, 712a, 713a, 714a, 715a coupled to the microcontroller 108 and a plurality of second distance sensors 711b, 712b, 713b, 714b, and 715b coupled to the microcontroller 108. The first distance sensors 711a-715a are longitudinally arranged on the outer side of the first shoulder strap 102a and are used to detect a plurality of first distances in the second direction D2 (for example, the right side of the wearer 199). Similarly, the second distance sensors 711b-715b are longitudinally arranged on the outer side of the second shoulder strap 102b and are used to detect a plurality of second distances in a fourth direction D4 (e.g., the left side of the wearer 199).

In the third embodiment, the microcontroller 108 can define the waving state of the wearer's right arm in accordance with the aforementioned first distances, which will be described with reference to FIG. 8.

Figure 8:
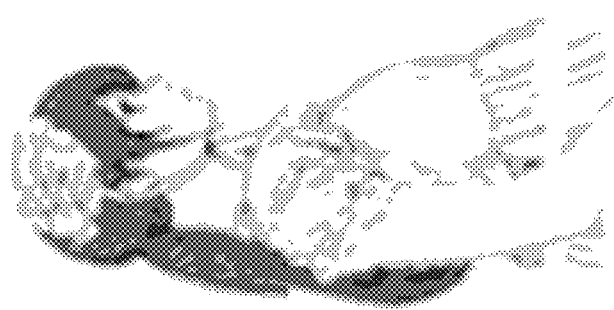
FIG. 8 is a schematic diagram of detecting a waving state of an arm according to the third embodiment of the present disclosure.
Figure 8:
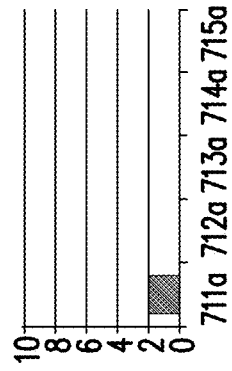
Figure 8:
Figure 8:
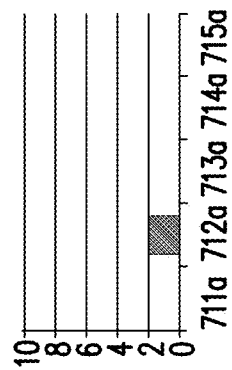
Figure 8:
Figure 8:
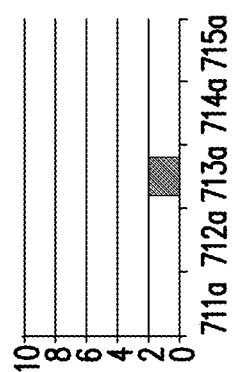
Figure 8:
Figure 8:
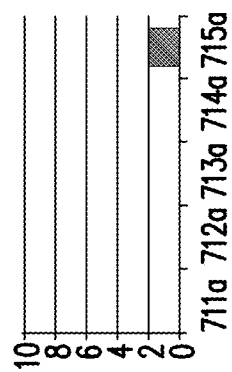

Please refer to FIG. 8, which is a schematic diagram of detecting a waving state of an arm according to the third embodiment of the present disclosure. In FIG. 8, it is assumed that the wearer is wearing the smart strap 100b (not shown) of FIG. 7B, and the movement of raising the right arm shown in FIG. 8 is sequentially performed from left to right. In this case, the first distance sensors 711a-715a will sequentially detect the first distances, so the microcontroller 108 can determine that the wearer has raised the right arm.

Similarly, the microcontroller 108 can also define the waving state of the left arm of the wearer according to the foregoing second distances, and the details thereof are similar to those shown in FIG. 8, which will not be repeated herein.

In the third embodiment, the microcontroller 108 can also define the are opening-and-closing state of the wearer's arms according to the first distances and the second distances, which will be described with reference to FIG. 9.

Figure 9:
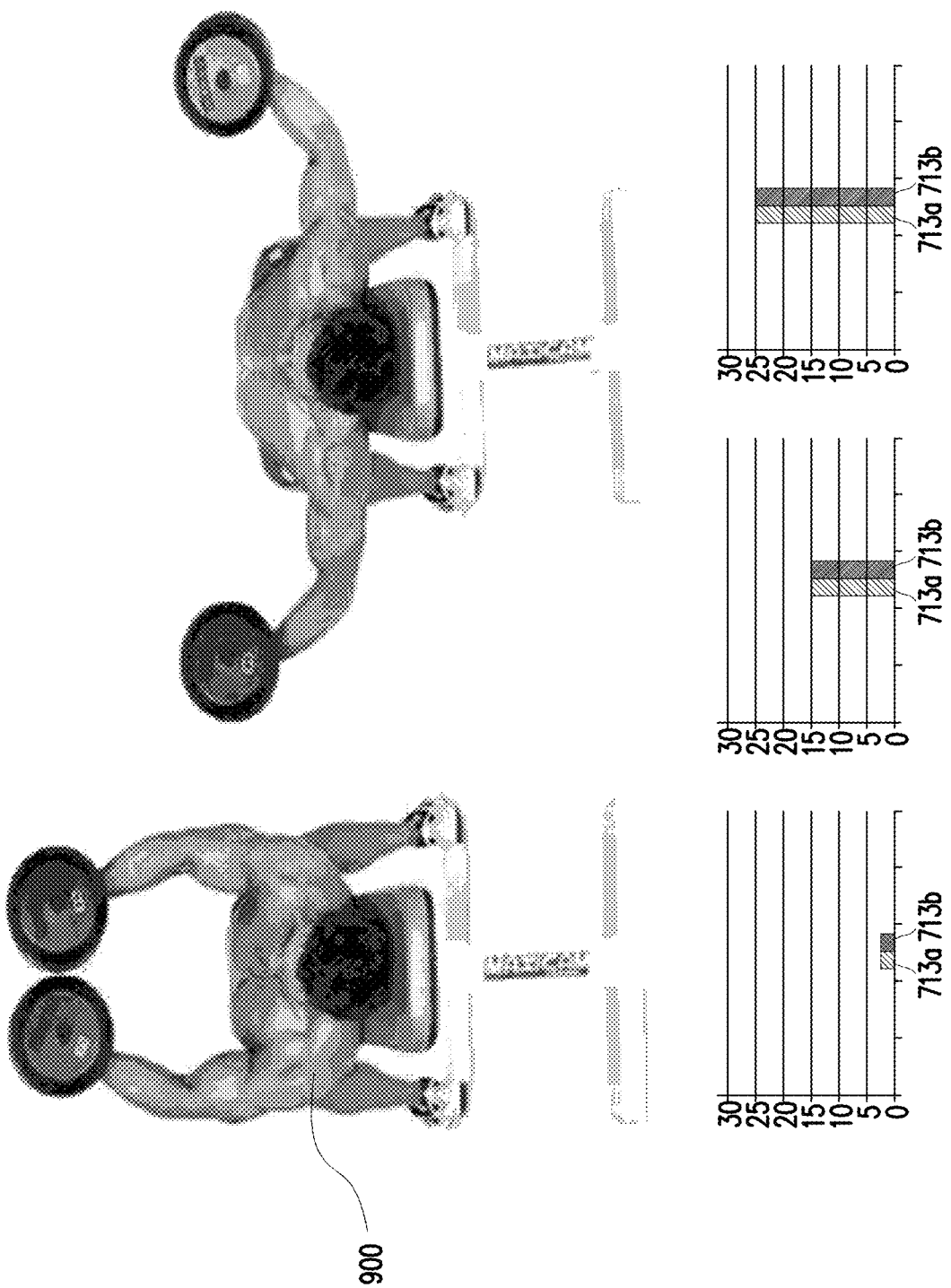
FIG. 9 is a schematic diagram of detecting the arm opening-and-closing state of the arm according to the third embodiment of the present disclosure.

Please refer to FIG. 9, which is a schematic diagram of detecting the arm opening-and-closing state of the arm according to the third embodiment of the present disclosure. In FIG. 9, it is assumed that the wearer 900 is wearing the smart strap 100b (not shown) of FIG. 7B, and the chest expanding movement shown in FIG. 9 is sequentially performed from left to right. Since the locations of the first distance sensor 713a and the second distance sensor 713b approximately corresponds to the initial position of the arms of the wearer 900 in FIG. 9 and are closer to the first shoulder strap 102a (not shown) and the second shoulder strap 102b (not shown), the first distance sensor 713a and the second distance sensor 713b can detect the shorter first distance and the second distance, respectively.

Then, during the process of the wearer 900 lowering the arms, since the arms of the wearer 900 will gradually move away from the first shoulder strap 102a and the second shoulder strap 102b, the first distance and the second distance respectively detected by the first distance sensor 713a and the second distance sensor 713b will gradually increase, as shown in FIG. 9. Correspondingly, the microcontroller 108 can know that the amines of the wearer 900 are currently open according to the variations of the first distance and the second distance.

Similarly, when the wearer 900 gradually closes the arms, the first distance and the second distance measured by the first distance sensor 713a and the second distance sensor 713b, respectively, will gradually decrease. Accordingly, the microcontroller 108 can know that the wearer 900 is gradually retracting the arms based on the variations of the first distance and the second distance.

As can be known from the above, the smart strap provided by the present disclosure can also detect the waving state and the arm opening-and-closing state of the wearer's arm through a column of distance sensors disposed on the outer side of the shoulder strap, thereby achieving the effects of upgrading the VR experience to AR or MR via the inside-out tracking technology.

In other embodiments, the first, second, and third embodiments may be combined to allow the smart strap to simultaneously have functions of detecting the distance of the object in front, detecting the human posture of the wearer (e.g., leg posture), and detecting the swinging state and the arm opening-and-closing state of the wearer's arm. The related details can be referred to the above embodiments, which will not be repeated herein.

Figure 10:
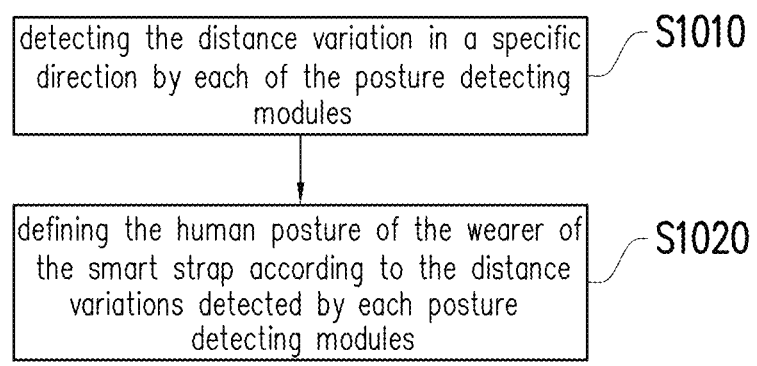
FIG. 10 is a flow chart of a method for defining a human posture according to an embodiment of the disclosure.

Please refer to FIG. 10, which is a flowchart of a method for defining a human posture according to an embodiment of the present disclosure. First, in step S1010, the distance variation in a specific direction can be detected by each of the posture detecting modules. Then, in step S1020, the human posture of the wearer of the smart strap can be defined according to the distance variations detected by each posture detecting module. For details of the steps of FIG. 10, reference may be made to the description in the above embodiments, and details will not be repeated herein.

In summary, the smart strap provided by the embodiment of the present disclosure can implement the distance detection of the object in the front, the human posture of the wearer (for example, the leg posture), and the waving state and the arm opening-and-closing state of the wearer's arm based on the inside-out tracking technology, so that the VR experience can be upgraded to AR or MR with a lower cost, lower environmental demand, low installing difficulty and high convenience.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims and their equivalents.

What is claimed is:

1. A smart strap, comprising:
   a first shoulder strap;
   a second shoulder strap;
   a chest strap, having a first end and a second end, wherein the first end of the chest strap is connected to the first shoulder strap, the second end of the chest strap is connected to the second shoulder strap, and the chest strap comprises a stiffness segment;
   at least one camera, disposed on a surface of the stiffness segment and facing a first direction, capturing a plurality of object images of an object in the first direction; and
   a microcontroller, connected to the at least one camera, receiving the object images from the at least one camera, detecting a distance between the object and the at least one camera based on the object images, and adjusting a screen shown to a wearer of the smart strap according to the distance;
   a plurality of posture detecting modules connected to the microcontroller, wherein the posture detecting modules are symmetrically disposed on the first shoulder strap and the second shoulder strap, or symmetrically disposed on the stiffness segment for detecting a human posture of the wearer of the smart strap,
   wherein each of the posture detecting modules comprises:
   a base, comprising a bottom surface, a side surface, and a top surface, wherein the bottom surface of the base is connected to a surface of the first shoulder strap, a surface of the second shoulder strap or a surface of the stiffness segment, and the top surface of the base faces the first direction;
   a knob, comprising a bottom surface, a side surface and a top surface, wherein the bottom surface of the knob is rotatably connected to the side surface of the base and the top surface of the knob faces a second direction, wherein the second direction is perpendicular to the first direction; and
   a distance sensor, disposed on the side surface of the knob and performs a distance detection in different directions according to the rotation of the knob.

2. The smart strap of claim 1, wherein the chest strap further comprises at least one elastic segment connected between the stiffness segment and at least one of the first shoulder strap and the second shoulder strap.

3. The smart strap of claim 1, wherein the microcontroller provides the distance to a host to accordingly adjust the screen shown to the wearer of the smart strap, wherein the screen is provided by a head mounted display worn by the wearer.

4. The smart strap of claim 1, wherein hen the wearer of the smart strap performs a specified movement, the distance sensor of each of the posture detecting modules detects a distance variation as a calibration reference value for defining the human posture of the wearer.

5. The smart sling of claim 1, wherein the posture detecting modules comprise:
   a first posture detecting module, disposed at a first location for detecting a first specific distance in a third direction and providing the first specific distance to the microcontroller;
   a second posture detecting module, disposed at a second location for detecting a second specific distance in the third direction and providing the second specific distance to the microcontroller, wherein the second location corresponds to the first location.

6. The smart strap of claim 5, wherein when the first specific distance and the second specific distance are both equal to a calibration reference value, the microcontroller determines that the human posture of the wearer is a standing posture.

7. The smart strap of claim 5, wherein the first location and the second location respectively corresponds to a right side and a left side of the wearer, and when the first specific distance is less than the second specific distance, the microcontroller determines that the wearer's right knee has been raised, and when the first specific distance is greater than the second specific distance, the microcontroller determines that the wearer's left knee has been raised.

8. The smart strap of claim 5, wherein the microcontroller changes a viewing angle of the screen shown to the wearer based on the first specific distance and the second specific distance.

9. The smart strap of claim 5, wherein the screen further comprises a plurality of visual aid grids, and the microcontroller adjusts a plurality of visual distances corresponding to the visual aid grids according to the first specific distance and the second specific distance.

10. The smart strap of claim 1, further comprising a plurality of first distance sensors connected to the microcontroller, longitudinally arranged on an outer side of the first shoulder strap, and configured to detect a plurality of first distances in a second direction, wherein the first shoulder strap is worn on a first side of the wearer, and the microcontroller defines a waving state of the wearer's arm on the first side according to the first distances.

11. The smart strap as claimed in claim 10, wherein:
when the first distance sensors sequentially detect the first distances from bottom to top, the microcontroller determines that the wearer's arm on the first side has swung upward;
when the first distance sensors sequentially detect the first distances from top to bottom, the microcontroller determines that the wearer's arm on the first side has swung downward.

12. The smart strap according to claim 10, further comprising a plurality of second distance sensors connected to the microcontroller, longitudinally arranged on an outer side of the second shoulder strap, and configured to detect a plurality of second distances in a fourth direction, wherein the second shoulder strap is worn on a second side of the wearer, the fourth direction is opposite to the second direction, and the microcontroller defines an arm opening-and-closing state of the wearer according to the first distances and the second distances.

13. A smart strap, comprising:
a first shoulder strap;
a second shoulder strap;
a chest strap, having a first end and a second end, wherein the first end of the chest strap is connected to the first shoulder strap, and the second end of the chest strap is connected to the second shoulder strap;
a plurality of posture detecting modules, symmetrically disposed on the first shoulder strap and the second shoulder strap, or symmetrically disposed on the chest strap, wherein each of the posture detecting modules is configured to detect a distance variation in a specific direction;
a microcontroller, connected to the posture detecting modules and defining a human posture of a wearer of the smart strap according to the distance variation detected by each of the posture detecting modules;
wherein the posture detecting module comprises:
a first posture detecting module, disposed at a first location for detecting a first specific distance in a third direction and providing the first specific distance to the microcontroller;
a second posture detecting module, disposed at a second location for detecting a second specific distance in the third direction and providing the second specific distance to the microcontroller, wherein the second location corresponds to the first location.

14. The smart strap of claim 13, wherein the first location and the second location respectively corresponds to a right side and a left side of the wearer, and when the first specific distance is less than the second specific distance, the microcontroller determines that the wearer's right knee has been raised, and when the first specific distance is greater than the second specific distance, the microcontroller determines that the wearer's left knee has been raised.

15. A smart strap, comprising:
a first shoulder strap;
a second shoulder strap;
a chest strap, having a first end and a second end, wherein the first end of the chest strap is connected to the first shoulder strap, and the second end of the chest strap is connected to the second shoulder strap,
a plurality of posture detecting modules, symmetrically disposed on the first shoulder strap and the second shoulder strap, or symmetrically disposed on the chest strap, wherein each of the posture detecting modules is configured to detect a distance variation in a specific direction;
a microcontroller, connected to the posture detecting modules and defining a human posture of a wearer of the smart strap according to the distance variation detected by each of the posture detecting modules;
a plurality of first distance sensors connected to the microcontroller, longitudinally arranged on an outer side of the first shoulder strap and configured to detect a plurality of first distances in a second direction, wherein the first shoulder strap is worn on a first side of the wearer, and the microcontroller defines a waving state of the wearer's arm on the first side according to the first distances.

16. The smart strap of claim 15, further comprising a plurality of second distance sensors connected to the microcontroller, longitudinally arranged on an outer side of the second shoulder strap and configured to detect a plurality of second distances in a third direction, wherein the second shoulder strap is worn on a second side of the wearer, the third direction is opposite to the second direction, and the microcontroller defines an arm opening-and-closing state of the wearer according to the first distances and the second distances.

* * * * *